(12) United States Patent
Chisholm et al.

(10) Patent No.: US 8,741,980 B2
(45) Date of Patent: Jun. 3, 2014

(54) HARDENABLE TWO PART ACRYLIC COMPOSITION

(75) Inventors: Michael Stephen Chisholm, County Durham (GB); David McDonald, Country Durham (GB); Sera Saheb Abed-Ali, Country Durham (GB)

(73) Assignee: Lucite International UK Limited, Hampshire (GB)

( * ) Notice: Subject to any disclaimer, the term of this patent is extended or adjusted under 35 U.S.C. 154(b) by 27 days.

(21) Appl. No.: 13/058,956

(22) PCT Filed: Aug. 13, 2009

(86) PCT No.: PCT/GB2009/051021
§ 371 (c)(1),
(2), (4) Date: Apr. 29, 2011

(87) PCT Pub. No.: WO2010/018412
PCT Pub. Date: Feb. 18, 2010

(65) Prior Publication Data
US 2011/0263739 A1     Oct. 27, 2011

(30) Foreign Application Priority Data

Aug. 14, 2008 (GB) .................................. 0814854.6
Mar. 6, 2009 (GB) .................................. 0903912.4

(51) Int. Cl.
*C08F 2/50* (2006.01)
*C08J 3/28* (2006.01)

(52) U.S. Cl.
USPC ........... 522/120; 522/109; 522/110; 522/113; 522/114; 522/178; 522/182; 522/153; 522/149; 522/150; 523/115; 523/116; 523/120; 524/533

(58) Field of Classification Search
USPC .................. 523/201, 115, 116, 120; 524/533; 525/902; 522/109, 110, 111, 112, 113, 522/114, 120
See application file for complete search history.

(56) References Cited

U.S. PATENT DOCUMENTS

| | | | |
|---|---|---|---|
| 4,268,639 A | 5/1981 | Seidel et al. | |
| 4,396,377 A | 8/1983 | Roemer et al. | |
| 4,698,373 A | 10/1987 | Tateosian et al. | |
| 4,929,495 A | 5/1990 | Stanislawczyk | |
| 5,650,108 A | 7/1997 | Nies et al. | |
| 5,880,207 A | 3/1999 | Delphin et al. | |
| 6,113,343 A * | 9/2000 | Goldenberg et al. | 414/729 |
| 6,133,343 A | 10/2000 | Hatanaka et al. | |
| 6,139,322 A | 10/2000 | Liu | |
| 2002/0072565 A1 | 6/2002 | Muranaka et al. | |
| 2006/0147714 A1 | 7/2006 | Schultes et al. | |
| 2006/0293451 A1 | 12/2006 | Schmitt et al. | |
| 2007/0032567 A1 | 2/2007 | Beyar et al. | |
| 2007/0213425 A1 | 9/2007 | Higham et al. | |
| 2007/0259987 A1 | 11/2007 | Schattka et al. | |
| 2010/0168271 A1 | 7/2010 | Beyar et al. | |

FOREIGN PATENT DOCUMENTS

| | | |
|---|---|---|
| CN | 1196923 A | 10/1998 |
| DE | 10339329 A1 | 3/2005 |
| EP | 0 583 926 A2 | 2/1994 |
| EP | 0614919 A1 | 9/1994 |
| EP | 1 046 658 B1 | 8/2005 |
| GB | 2 347 679 A | 9/2000 |
| JP | A 2005281548 | 10/2005 |
| JP | A 2006316239 | 11/2006 |
| JP | 2007503482 A | 2/2007 |
| SU | 1815264 A1 | 2/1991 |
| WO | WO 82/02556 A | 8/1982 |
| WO | WO 2008/032322 A2 | 3/2008 |

OTHER PUBLICATIONS

Alder et al. Freeze Coagulation of ABS Latex. Industrial & Engineering Chemisty Research, 1997, 36(6), 2156-2162.*
Oct. 5, 2009 Search Report issued in PCT/GB2009051021.
International Preliminary Report on Patentability and Written Opinion issued in PCT/GB2009/051021 on Feb. 15, 2011.
The Second Office Action for CN Patent Application No. 200980131088.8 for Lucite International UK Limited dated Mar. 7, 2013.
Notification of Reason for Rejection 2011-522555 dated Apr. 30, 2013 Patent Attoreny Hironori Onda, et al.
Office Action for Application Patent No. 2011109208/4(013395) date of filing. Mar. 11, 2011 for Lucite International UK Limited Queens Gate.

* cited by examiner

*Primary Examiner* — Sanza McClendon
(74) *Attorney, Agent, or Firm* — Shumaker, Loop & Kendrick, LLP

(57) ABSTRACT

A hardenable two part acrylic composition, a polymer component of the two part hardenable composition and a method of producing a polymer component of the two part composition are disclosed. The hardenable two part acrylic composition includes an acrylic polymer composition first part and an acrylic monomer composition second part. The acrylic polymer composition first part includes a first type of acrylic polymer particles wherein each first type of acrylic polymer particle is formed of a network of coalesced emulsion polymerized acrylic microparticles or is macroporous. The acrylic polymer composition may include emulsion polymerised acrylic polymer particles of particle size between 10 and 2000 nm and includes the use of acrylic polymer particles formed of a network of coalesced emulsion polymerized acrylic microparticles as a dough time reduction agent in a hardenable two part acrylic composition.

29 Claims, 2 Drawing Sheets

Figures 1a and b SEMs of the spray dried emulsion
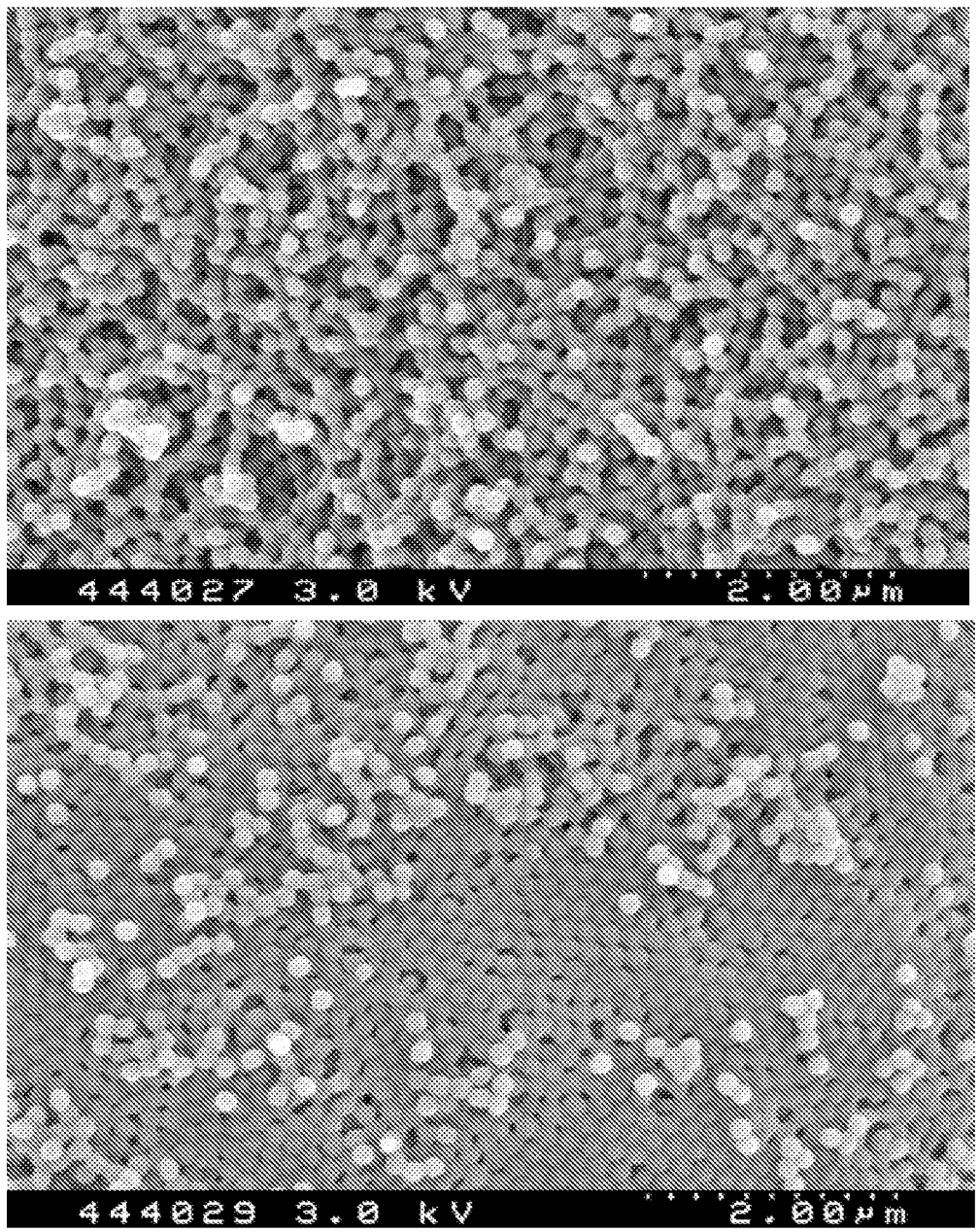

Figures 2a and b SEMs of coagulated, filtered, washed and dried emulsion
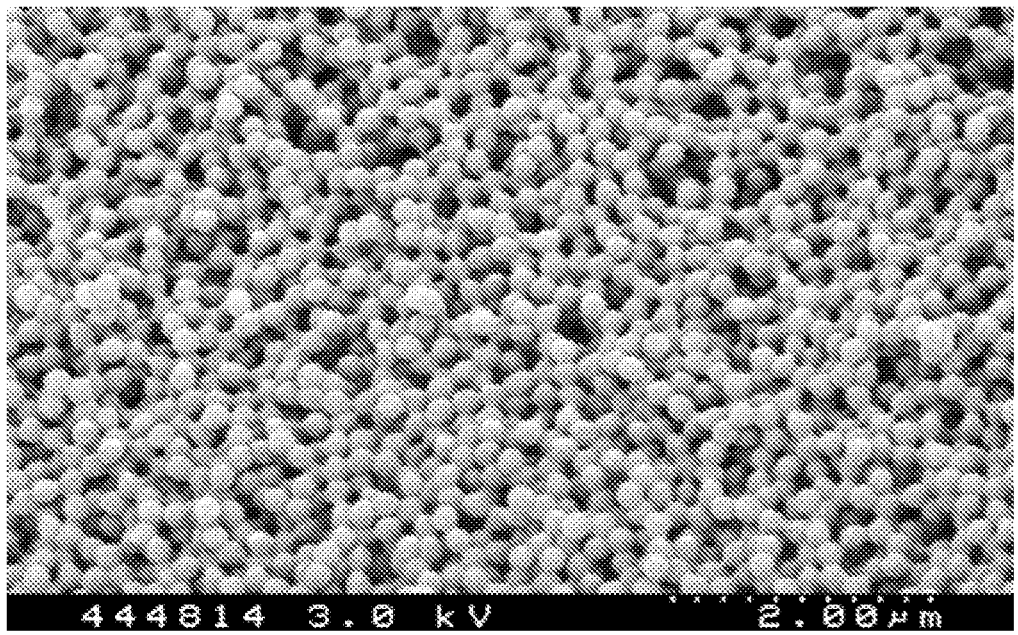
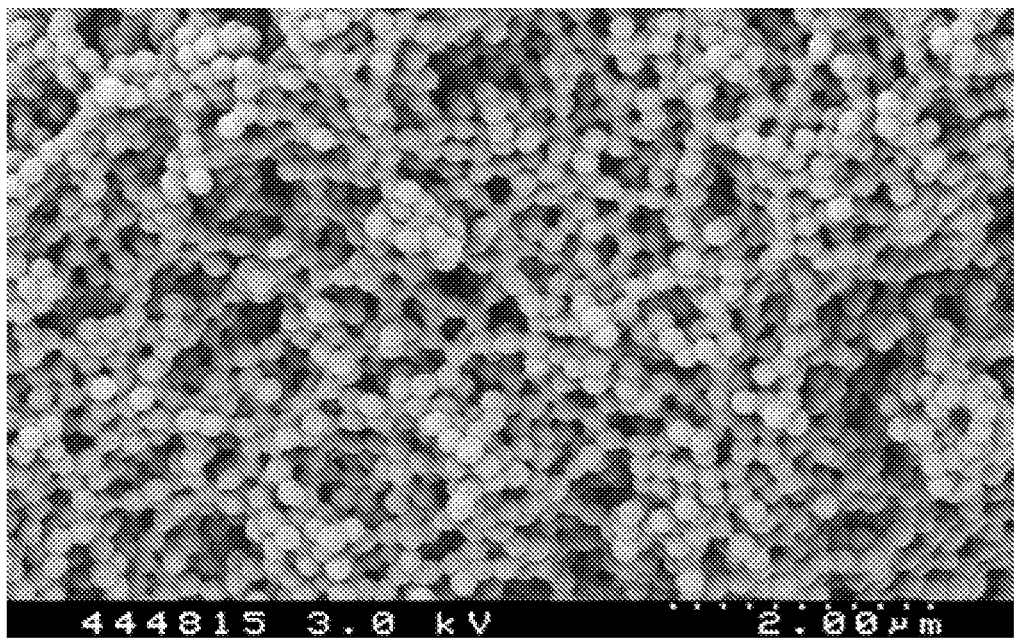

HARDENABLE TWO PART ACRYLIC COMPOSITION

The present invention relates to a polymer composition, in particular but not exclusively, a hardenable two part acrylic composition, a polymer component of the two part hardenable composition and a method of producing a polymer component of the two part composition.

Hardenable compositions formed by mixing together acrylic polymers and monomers are useful in a wide range of applications. Particular utility is found in dental, medical, adhesive and construction applications, where such materials have been used for over 40 years.

Dental applications include their use in denture bases, denture base plates, denture liners, denture repairs, custom trays, veneering for crowns and bridgework, artificial teeth, veneers and repair for natural teeth and tooth restorative fillings.

Medical applications include their use as bone cements. Bone cements find applications generally in the filling of bone cavities and in particular, as prosthetic cements, cranial cements, vertebral cements in vertebroplasty and in the production of shaped articles that harden extra-corporeally and which can then be introduced into the body.

Adhesive and construction applications include numerous applications such as their use in jointing, cementing, gap filling and in the formation of porous materials.

Hardenable acrylic compositions are generally composed of a solid component and liquid component. The solid component comprises a powder formed from polymer particles and, if appropriate, further additives, such as polymerisation initiators and catalysts, fillers and dyestuffs. The liquid component comprises a liquid monomer or monomers and further additives, such as accelerators and stabilisers. When ready for use, the solid and liquid components are mixed together to form a liquid or semi-solid paste, which, under the action of the polymerisation initiators and accelerators, increases in viscosity and hardens into a solid.

The solid component typically used consists of small spherical beads (usually about 20-150 microns in diameter) of poly(methyl methacrylate) (PMMA) and a small amount of polymerisation initiator such as dibenzoyl peroxide (BPO), usually encapsulated within the PMMA bead, but which can also be added as a separate component. The liquid component is usually a monomer, typically methyl methacrylate (MMA), which may also contain a polymerisation activator such as N,N-dimethyl-p-toluidine (a tertiary amine) (DMPT) and an inhibitor such as hydroquinone (HQ) to prevent the monomer from spontaneously polymerising.

When the solid and liquid components are mixed together, the polymer particles are wetted with monomer, solvated and begin to dissolve. The solvated polymer particles release dibenzoyl peroxide initiator into the monomer which interacts with activator, if present, to produce radicals that react with the monomer and initiate room temperature addition polymerisation of the monomer. The mixture starts out at a relatively low viscosity and progresses to a stiffer and stiffer system that eventually hardens completely.

This constantly changing viscosity of the mixture is characterised by dough, work and set times. The dough time is considered to be the length of time following the start of mixing for the mixture to achieve a dough-like mass that does not stick or adhere to the walls of a polypropylene mixing beaker and can be removed in one piece using a spatula. The set time is determined by forming the dough into a sausage shape and occasionally tapping it against a hard surface. The set time is considered to be the time from the start of mixing to the point at which the mixture is transformed into a hard mass that does not deform and gives a noticeable change in the sound produced when tapped against a hard surface. The work time is determined by occasionally bringing two pieces of dough gently together and pulling them apart. The time at which the two pieces of dough no longer stick together is noted. The work time is calculated by subtracting the dough time from the time taken from the start of mixing for the two pieces of dough to stop sticking together.

The dough, work and set times are very important parameters that determine how the hardenable compositions are to be used. Compositions hardenable at room temperature (so-called "self-curing" or "cold-curing" systems) have dough times that are typically 4 to 10 minutes and set times that are typically 10 to 25 minutes in duration. The work time effectively defines the time period available for the operator to manipulate the dough in the desired fashion, for example pressing into a denture mould for denture base manufacture, or pressing into a bone cavity during hip repair or replacement or injecting into a vertebral cavity during spinal surgery or forcing into a gap or cavity during industrial cementing operations. There is an obvious desire to maximise the work time available to the operator. This should ideally be achieved without an increase in the set time as this defines the end point for the cementing or fixing operation. This therefore focuses attention on shortening the dough time. The dough time is determined by the rate at which the combination of solid and liquid components rise in viscosity immediately after mixing and is controlled by a number of factors, such as polymer bead particle size and shape, polymer molecular weight, and polymer composition.

U.S. Pat. No. 5,650,108 (Nies et al) describes use of a bead mill to treat a mixture of PMMA beads and granules. The resulting polymer mixture is then stirred with the liquid component to yield a composition that doughs after about 2 minutes.

US2007/0213425 A1 (Higham and He) teaches the use of a ball mill or jet mill to produce milled PMMA or PMMA copolymer beads that display shortened dough times compared to the unmilled beads after mixing with the liquid component of a bone cement.

U.S. Pat. No. 4,268,639 (Seidel et al) describes fast doughing self-curing compositions based on mixtures of PMMA and poly(2-hydroxyethyl methacrylate) (PHEMA) as the solid component and MMA and/or 2-hydroxyethyl methacrylate (HEMA) as liquid component. Dough times as short as 2 minutes and work times of at least 6 minutes are described.

US2007/0032567 A1 (Beyar et al) describes fast doughing bone cement compositions that reach a viscosity of at least 500 Pascal seconds within 180 seconds after mixing monomer and polymer components, and a working window of at least 5 minutes. The characteristics are said to be obtained through the use of beads of different size distributions. The beads less than 20 microns in diameter are said to facilitate rapid wetting with monomer liquid and contribute to a fast transition to a viscous state.

The influence of PMMA bead size on the rheological properties of bone cements has been studied by Hernandez, L.; Goni, I.; Gurruchaga, M., "Effect of size of pmma beads on setting parameters and rheological properties of injectable bone cements", Transactions—7th World Biomaterials Congress, Sydney, Australia, 17 May 2004-21 May 2004, p 740. The authors note that "With increasing the fraction of small beads . . . , the onset of the increasing viscosity appears sooner. This is due to the solvation of the smallest PMMA beads (<20 microns), which causes an increase of viscosity of the polymerizing mass". Also, "In conclusion, we can say that it is feasible to obtain injectable bone cements with optimal rheological properties by means of mixing beads of different sizes".

Another paper that describes how the rheological properties of acrylic bone cement are influenced by the PMMA bead particle size is: Lewis G. and Carroll M, J Biomed Mater Res (Appl Biomater) 63: 191-199, 2002. The authors conclude that one of the factors that strongly influence the rheological properties is the relative amount of small-sized PMMA beads (mean diameter between 0 and 40 microns).

A study on the doughing time of heat-cured dental resins (McCabe, J. F., Spence D. and Wilson H. J., Journal of Oral Rehabilitation, 1975 Volume 2, pages 199-207) concluded that " . . . the concept of short doughing time depends upon the presence of considerable numbers of small beads." The particle diameter of small beads is inferred as D<20 microns.

From the above description, it can be seen that the most commonly described methods of achieving short dough time are to subject the PMMA polymer particles to milling or to deliberately incorporate a significant proportion of PMMA polymer particles of <20 microns in diameter into the solid component of the hardenable composition. Milling processes suffer from the disadvantages of being limited in the amount of beads that can be milled at one time, leading to long manufacturing times if significant quantities of material are involved. Additionally, the problems of batch to batch reproducibility, cleaning the mill between batches and introduction of contamination during the significant amount of processing and manual handling need to be overcome. Controlling the relative amount of <20 microns diameter PMMA polymer particles in the solid component is not straightforward. PMMA beads used in hardenable compositions are generally produced by a suspension or dispersion polymerisation process. This involves polymerizing dispersed MMA monomer droplets in a liquid phase, usually water, to form solid spherical beads, which are then separated from the liquid phase by a filtration step, washed to remove dispersing agents, dried and then sieved. However, particles <20 microns diameter are relatively difficult to filter and wash, involving long and often laborious processing times.

An alternative means of collecting a significant proportion of small (<20 microns diameter) PMMA polymer particles is use of a sieving process to separate out the smallest particle size fraction from a conventionally prepared suspension polymerisation slurry. However, the yields are relatively low, sieving times can be long and the problem remains of what to do with the rather large amount of coarser particle size material that is retained on the sieves.

Another approach to generating a significant proportion of small (<20 microns diameter) PMMA polymer particles is to use mechanical methods to break down the beads of a conventionally produced material, e.g., by milling, grinding, crushing, etc. However, PMMA beads are relatively hard and so long processing times are usually required to achieve significant increase in the proportion of small (<20 microns diameter) PMMA polymer particles (typically >24 hours for ball milling). Additionally, the batch to batch repeatability of such a process is quite poor, sometimes necessitating further processing of the resultant product, e.g., by sieving or blending, to achieve the desired particle size distribution.

This makes the commercial manufacture of PMMA with a significant proportion of particles <20 microns in diameter an expensive and sometimes tedious and unreliable undertaking.

One object of the present invention is to provide alternative solutions which avoid one or more of the above problems.

According to a first aspect of the present invention there is provided a hardenable two part acrylic composition comprising an acrylic polymer composition first part and an acrylic monomer composition second part, the acrylic polymer composition comprising a first type of acrylic polymer particles characterized in that each first type of acrylic polymer particle is formed of a network of coalesced emulsion polymerized acrylic microparticles.

By coalesced is not meant that the individual microparticles merge completely but that they join together sufficiently to form a larger first type of particle. Typically, the microparticles come into close contact but also retain individual character.

Preferably, the acrylic polymer composition also comprises at least one further type of acrylic polymer particles. Preferably, the at least one further type(s) of acrylic polymer particles are polymer beads. Such beads are not formed of a network of coalesced emulsion polymerized microparticles but are preferably produced by conventional polymer processing. Such polymer beads are well known to the skilled person in the field of acrylic polymer compositions and may, for example, be those made by bulk, solution or suspension polymerization. Typically, the beads are made by suspension polymerization. There may be more than one further type of acrylic polymer particles in the acrylic polymer composition which are differentiated from each other by average particle size and/or molecular weight. For instance there may be two, three or four such further types of acrylic polymer particles.

The term beads as used herein is not meant to be interpreted restrictively unless indicated otherwise and refers to a discrete polymer particle of any suitable size, shape and surface texture.

Typically, the total of first and, if present, further types of polymer particles form at least 98% of the polymer present in the acrylic polymer composition, more preferably, at least 99%, most preferably, approximately 100% of the polymer present in the acrylic polymer composition. The total of first and, if present, further types of polymer particles typically form between 50-99.9% w/w of the acrylic polymer composition, more preferably, 60-97.5% w/w, most preferably, 65-94.5% w/w. The balance is generally made up of filler, dyestuffs, catalysts and initiator, although residual emulsifier may also be present.

Typically, the level of filler in the acrylic polymer composition is 0-49.9% w/w of the acrylic polymer composition, more preferably, 2-39.9% w/w, most preferably, 5-34.9% w/w. The total level of unreacted initiator, whether residual or added, in the acrylic polymer composition is typically, 0.1-5% w/w of the acrylic polymer composition, preferably, 0.2-4% w/w, more preferably, 0.4-3.5% w/w.

The initiator may be present in both the first and, if present, further types of polymer particles that form the acrylic polymer composition. The initiator in the first and, if present, further polymer particles is the residual amount of unreacted initiator used in the formation of the particles which is therefore the equivalent of the excess amount of initiator. Some initiator can alternatively or additionally be added as a separate component to the two part composition. In the emulsion polymerized acrylic microparticles, the level of residual initiator present before reaction with the second part is typically, 0.001-10% w/w of the emulsion polymerized acrylic microparticles, preferably, 0.1-5% w/w, more preferably 0.1-3% w/w. Alternatively, the level of initiator is preferably 0.1-6% w/w, more preferably 0.1-5% w/w.

Preferably, the Z-average particle size of the emulsion polymerized microparticles which form a coalesced network to make up the larger acrylic polymer particle of the invention is less than 2000 nm as determined by light scattering using a Malvern Zetasizer nano series S particle size analyzer (adding one drop of emulsion to 1 ml of deionised water in a measurement cuvette, allowing the test sample to equilibrate at 25° C. and determining Z-average particle size using the software provided by the instrument), more preferably, less than 1000 nm, most preferably, less than 800 nm, especially, less than 500 nm. A preferred Z-average particle size range for the emulsion polymerized microparticles is between 10-2000 nm, more preferably, 20-1000 nm, most preferably, 50-500 nm, especially 150-450 nm, as determined by light scattering using a Malvern Zetasizer as above.

Typically, the emulsion polymerized microparticles may be single stage or multistage i.e. the so called core/shell microparticles. In this regard, it may be adequate to use a single monomer such as methyl methacrylate for making seed, core and shell. In this case, particularly if the composition and molecular weight of the seed, core and shell are designed to be the same, standard single stage emulsion polymerization techniques known to the skilled person could be deployed. However, to obtain emulsion particles that display some control over their structure, particularly their composition, particle size and molecular weight, it is preferable to use the multistage core-shell emulsion polymerization approach.

For manufacturing core-shell particles by emulsion polymerization, it is convenient to employ the widely used method of initially forming seed particles, which then act as nuclei for further growth, i.e. to produce a polymeric core and then shell. The concept is described in more detail by V. L. Dimonie, et al, "Emulsion Polymerization and Emulsion Polymers", P. A. Lovell and M. S. El-Aasser, Eds, John Wiley & Sons Ltd, Chapter 9, pages 294-326, (1997). The seed particles may be formed and stabilised using either emulsifier-free techniques (i.e., particle stabilisation arising from the use of ionic water-soluble initiators, such as potassium, sodium or ammonium persulphate) or through using emulsifiers. Once the seed particles are formed, the core and shell are formed from sequential addition of further aliquots of monomer and initiator.

In a particularly preferred embodiment, the emulsion microparticles incorporate the initiator in their polymer matrix. Accordingly, in this embodiment, the initiator is not added separately to the first type of polymer particles of the invention.

Advantageously, the initiator for the hardenable composition can be added as excess initiator during the emulsion polymerisation of the microparticles so that some initiator is used in the polymerisation of the emulsion particles but as the emulsion particles form, the excess initiator is incorporated into the polymer matrix. Subsequently, after wetting and dissolution with monomer, the initiator is released and thus able to initiate the hardening phase. In a core/shell particle, the initiator is preferably incorporated in the outer shell i.e. during the final stage of the multistage emulsion polymerisation process and, accordingly, excess initiator is used in the final shell polymerisation stage. During polymerization of the first or further type of polymer particle more than one initiator may also be used. In the case of multiple initiators, it is advantageous for one of the initiators to be substantially used up in the polymerization and a second initiator to be in excess and only partly used so that the excess amount of the second initiator is incorporated into the particles. This procedure may be assisted by the initiators having different half lives so that a shorter half life initiator (i.e., an initiator with a higher decomposition rate at a given temperature and reaction medium) is used up preferentially. In addition, a higher temperature can be used to drive the polymerization to completion in the presence of the first initiator whilst a lower temperature can retard polymerization of monomer in the presence of the second initiator intended as a residual initiator. However, some of the second initiator will inevitably be used up because to incorporate the initiator into the particle some polymerization must take place in the presence of the second initiator. Whether one or more initiators are used, the amount of initiator left as residue depends on the time of exposure of the initiator to polymerization conditions and reactants, and the relative reactivity to the first initiator, if present. It will be appreciated by the skilled person that the exact amount of residual initiator will be dependent on the experimental conditions and can easily be determined by trial and error and then be made reproducible by careful control of quantities of monomers and initiators and process conditions. The time of addition of the initiator in excess is also relevant to the molecular weight of the polymer. If added too early in the polymerization, the molecular weight of the particle will be reduced. Accordingly, the molecular weight required will also influence the time of addition of the initiator in excess so that the excess initiator is incorporated whilst achieving the molecular weight required for the particular application.

For the avoidance of doubt, by "excess initiator" is meant, the portion of initiator that is not required to complete polymerisation of the acrylic polymer particles and is available for subsequent reaction after the initial polymerisation of the acrylic polymer particles is terminated.

Advantageously, the network of coalesced emulsion polymerized microparticles form a porous acrylic polymer particle, more preferably, a microporous acrylic polymer particle.

By microporous in the present invention is meant having an average pore size of between 0.1 and 2000 nm, more preferably, between 1-1000 nm, most preferably, 10-500 nm. Pore size may be determined by scanning electron microscopy (SEM) according to the following test method: Sprinkle the sample of acrylic polymer particles onto a conducting self-adhesive carbon tab on a standard aluminium SEM stub. Coat the sample with a thin layer of metal (Pt) by vacuum metallization to avoid charging in the SEM instrument. SEM images are taken using a Hitachi 54500 Field Emission SEM using accelerating voltage of 3 kV and working distance of 20 mm. Imaging is carried out on several particles and representative images obtained at different magnifications.

Typically, the size of the first type of acrylic polymer particle of the invention is not thought to be critical but will clearly be in excess of the size of the emulsion microparticles. Typically, the first type of acrylic particles of the invention have an average particle size of 1-300 microns, more typically, 2-200 microns, most typically, 5-200 microns, especially, 5-150 microns. However, the size of the particles of the invention is thought to be less critical than the emulsion polymerized microparticles which make up their structure. Surprisingly, the use of the first type of acrylic polymer particle in a hardenable composition gives a reduced dough time.

Typically, the acrylic first type of polymer particles of the invention are formed by drying of the liquid emulsion to form a powder.

The preferred means of drying the emulsion polymer microparticles is to use spray drying. However, other methods of direct drying of the emulsion polymer are also possible e.g., vacuum paddle or rotational drying. Additionally, the emulsion could be coagulated through use of ionic salts (e.g., magnesium sulphate, calcium chloride, aluminium sulphate, etc), then filtered, washed and dried. All these techniques will cause the emulsion microparticles to coalesce into larger particles. Surprisingly, it has been found that the use of these larger particles in a hardenable composition significantly shortens the dough time. The use of particles so formed had not been expected to cause such an improvement. The coalescing of the emulsion microparticles does not cause them to merge completely and instead they form a network of joined particles. These drying techniques and the prior emulsion polymerization allow very careful control of the microparticle and first type particle size which gives easy reproducibility and reduces batch to batch variation.

By drying is meant reduction of the moisture content of the emulsion microparticles to <10% w/w, more preferably, <5% w/w, most preferably, <2% w/w.

If more than one type of acrylic polymer particle is present, the different types of polymer particles are blended together to form the acrylic polymer composition, typically, in the presence of suitable other polymer composition components known to the skilled person. Such polymer composition additives include initiators, catalysts, dyestuffs and fillers.

Blending the first type of polymer particles of the invention with further polymer particles may be carried out by any suitable technique known to the skilled person for blending different sized particles.

However, the preferred means of blending small and larger polymer particles is through conventional tumble blending methods. Other methods of blending powders are also possible, e.g., screw blending and roll blending.

Initiators that can be used to initiate the emulsion polymerization are persulphates, (e.g., potassium, sodium or ammonium), peroxides (e.g, hydrogen peroxide, dibenzoyl peroxide, tert-butylhydroperoxide, tert-amylhydroperoxide, di-(2-ethylhexylperoxydicarbonate or lauroyl peroxide) and azo initiators (e.g., 4,4'-azobis(4-cyanovaleric acid)).

Initiators are also present in the polymer composition to initiate the hardening process. In addition to the emulsion initiators above, a particularly preferred initiator for this stage is dibenzoyl peroxide.

Emulsifiers that can be used in the emulsion polymerization are those that are typical in conventional emulsion polymerization, including anionic (e.g., sodium dioctyl sulfosuccinate, disodium ethoxylated alcohol half ester of sulfosuccinic acid, tetrasodium N-(1,2-dicarboxy ethyl)-N-octadecyl sulfosuccinate, sodium salt of sulphated alkylphenol ethoxylates, sodium alkane sulfonate, sodium dodecyl sulphate or sodium 2-ethylhexyl sulphate), nonionic (e.g., polyethylene glycol nonylphenyl ethers, polyethylene oxide octylphenyl ethers, or difunctional ethylene oxide/propylene oxide block copolymers) or cationic emulsifiers (e.g., hexadecyltrimethylammonium bromide or alkyl polyglycoletherammonium methyl chloride). Reactive or polymerizable emulsifiers or surfactants suitable for use with acrylic emulsions can also be used, e.g., sodium dodecylallyl sulfosuccinate, styrene sodium dodecylsulfonate ether, dodecyl sodium ethylsulfonate methacrylamide, methacrylic or vinylbenzyl macromonomers of polyethylene oxide or ethylene oxide/propylene oxide block copolymers or methacryloylethyl-hexadecyldimethylammonium bromide.

Preferably, the Z-average particle size of the resultant emulsion polymerized microparticles is less than 2000 nm as determined by light scattering, more preferably, less than 1000 nm, most preferably, less than 800 nm, especially, less than 500 nm. A preferred Z-average particle size range for the emulsion polymerized microparticles is between 10-2000 nm, more preferably, 20-1000 nm, most preferably, 50-500 nm, especially 150-450 nm, as determined by light scattering.

The core shell (C:S) ratio of the emulsion microparticles is typically, between C:S 95:5% wt and C:S 40:60% wt, more typically, between C:S 90:10% wt and C:S 50:50% wt, preferably, between C:S 85:15% wt and C:S 70:30% wt.

The % wt solids content of the emulsion before drying is typically, between 5 and 45% wt, more typically, between 7.5 and 40% wt, preferably, between 10 and 37.5% wt.

The weight average molecular weight (Mw) of the emulsion microparticles is typically, between 25,000 daltons and 3,000,000 daltons, more typically, between 100,000 daltons and 1,500,000 daltons, preferably, between 250,000 and 1000000, for instance, between 250,000 and 600,000. Molecular weight may be determined for this purpose by gel permeation chromatography (GPC).

Initiators that can be used for emulsifier free emulsion polymerisation include:—ionic water-soluble initiators, such as potassium, sodium or ammonium persulphate.

In medical and some dental applications, the filler is advantageously an x-ray opaque filler so that it can be observed during treatment or surgery by x-ray. Suitable fillers for this purpose include barium sulphate and zirconium dioxide, either encapsulated within the polymer particles or free. In the production of dentures or in industrial applications, other fillers may instead be used and these will be known to the skilled person in the art of such fields. Additionally, organic x-ray opaque monomers can be used instead of fillers. These can be copolymerized into any of the acrylic polymer particles during their production or incorporated into the acrylic monomer composition. Typical organic x-ray opaque monomers include halogenated methacrylates or acrylates, e.g., 2,3-dibromopropyl methacrylate or 2-methacryloyloxyethyl-2,3,5-triiodobenzoate.

As mentioned above, the polymer composition of the invention may include further types of acrylic polymer particles.

The method of manufacture of such further particles is generally conventional suspension or dispersion polymerization to produce generally spherical polymer particles, or beads. However, other methods of manufacture are also possible, e.g., bulk polymerization or solution polymerization followed by evaporation of the solvent.

By acrylic polymer herein whether in relation to the first or at least one further type of acrylic polymer is meant independently for each type a homopolymer of a polyalkyl(alk)acrylate or (alk)acrylic acid or copolymers of a polyalkyl(alk)acrylate or (alk)acrylic acid with one or more other vinyl monomers. Typically, a homopolymer of methyl methacrylate or a copolymer of methyl methacrylate with one or more other vinyl monomers is used. By other vinyl monomers is meant a further polyalkyl(alk)acrylate or (alk)acrylic acid such as ethyl methacrylate, methyl acrylate, ethyl acrylate, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, methacrylic acid, acrylic acid; hydroxyl-functional acrylates such as 2-hydroxyethyl methacrylate, hydroxypropylethyl methacrylate, 2-hydroxyethyl acrylate, or hydroxypropyl acrylate, vinyl compounds such as styrene, vinyl pyrrolidinone, vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate and 1,6-hexanediol diacrylate, particularly the compatible acrylic crosslinking monomers.

Crosslinking monomers can be used to crosslink one of the types of acrylic polymer particle. For the emulsion polymerized microparticles, crosslinking may be carried out in the core and the shell, or only the core, or only the shell.

Crosslinking serves the purpose of fine tuning the properties of the hardenable two part acrylic composition.

By acrylic monomer herein is meant any suitable alkyl(alk) acrylate or (alk)acrylic acid such as methyl methacrylate, ethyl methacrylate, methyl acrylate, ethyl acrylate, methacrylic acid or acrylic acid, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, hydroxyl-functional acrylates such as 2-hydroxyethyl methacrylate, hydroxypropylethyl methacrylate, 2-hydroxyethyl acrylate, or hydroxypropyl acrylate, vinyl compounds such as styrene, vinyl pyrrolidinone, vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate and 1,6-hexanediol diacrylate, particularly the compatible acrylic crosslinking monomers. Typically, methyl methacrylate is used.

The acrylic monomer composition of the invention is typically one or more monomers as defined above with, optionally, a suitable inhibitor such as hydroquinone (HQ), methyl hydroquinone (MeHQ), 2,6-di-tertiary-butyl-4-methoxyphenol (Topanol O) and 2,4-dimethyl-6-tertiary-butyl phenol (Topanol A). The inhibitor is present to prevent the monomer from spontaneously polymerising. Polymerisation activators or accelerators may also be optionally present, such as N,N-dimethyl-p-toluidine (DMPT) and N,N-dihydroxyethyl-p-toluidine (DHEPT) (both tertiary amines) or organic-soluble transition metal catalysts. The presence of activators or accelerators depends upon the final application. Where "cold-cure" is necessary such as in dental or bone cement applications, an accelerator is usually necessary. However, for industrial applications the use of heat in "heat-cure" systems is also possible. For instance, dentures can be activated by heat.

By alkyl herein is meant $C_1$-$C_{18}$ alkyl wherein the term alkyl and alk encompasses cyclooalkyl and hydroxyl functional $C_1$-$C_{18}$ alkyl. By alk herein is meant $C_0$-$C_8$ alk.

According to a second aspect of the present invention, there is provided a hardenable two part acrylic composition comprising an acrylic polymer composition first part and an acrylic monomer composition second part, the acrylic polymer composition comprising acrylic polymer particles, wherein at least a first type of acrylic polymer particle is microporous.

Typically, as mentioned above, the emulsion polymerized microparticles of the first aspect of the present invention are coalesced by drying a polymer emulsion of the particles such as by spray drying, paddle drying, oven drying or drying following coagulation and filtration. Advantageously, spray drying allows easy control of the final particle size by varying the spray droplet size appropriately. In any case, the drying step causes the emulsion particles to coalesce and form a network of emulsion particles, typically giving a porous larger particle. Typically, it has been found that emulsion polymerized particles can coalesce into a loosely hexagonal close packed matrix generally in the same plane but, in the present case, due to holes and imperfections in this arrangement and also the three dimensional structure of the particulate network, a porous macrostructure results. The emulsion polymerized particles may also, inevitably, be present in the coalesced network of the larger powder particle, in smaller clusters and also as individual particles. However, most of the particles are present as part of a coalesced network in the larger particles. For the avoidance of doubt, the presence of free emulsion polymerized particles which do not form part of such a network are not considered to be the first type of acrylic polymer particles in accordance with the invention and, if present, merely make up part of the balance of total polymer present in the acrylic polymer composition first part. In any case, the presence of the coalesced network of emulsion polymerized particles causes a surprising reduction in the doughing time of the hardenable composition. In addition, the solution provides very effective control over the doughing time so that any further types of particles in the composition can be used to obtain the necessary working and set time. This means it is easier to control the various parameters because only one particle component is necessary to control dough time. In prior art systems, it is necessary to use more than one type of particle just to control dough time so that simultaneously controlling working and set time can be very complicated. Accordingly, the invention simplifies the composition of the prior art.

In one preferred embodiment, the acrylic polymer composition comprises the first type of polymer particles and only a single type of further acrylic polymer particle, the former to control the dough time and the latter to control the working time.

According to a third aspect of the present invention, there is provided a hardenable two part acrylic composition comprising an acrylic polymer composition first part and an acrylic monomer composition second part, the acrylic polymer composition comprising emulsion polymerised acrylic polymer particles of particle size between 10 and 2000 nm.

The exact size of the emulsion polymerized particles in the coalesced and dried larger first type of particle is difficult to determine because they tend to pack into a matrix with other particles upon drying and, as mentioned above, may form a hexagonal close packing or other arrangement. Nevertheless, the microparticles are still clearly defined in their coalesced form. Notwithstanding this, their particle size in the larger first type of particle is more difficult to determine. However, by inspection of SEM results their size can be clearly estimated. Typically, the average size of the individual coalesced emulsion polymerized particles is 10-2000 nm, more typically, 50-500 nm, most typically 150-450 nm. As mentioned above, the emulsion polymerized acrylic polymer microparticles are typically coalesced into a larger acrylic polymer particle produced by drying of the emulsion. Accordingly, the emulsion particles form a microporous particle in their coalesced form.

By microparticles herein is meant particles that are smaller than the first type of acrylic polymer particles and no other restriction should be interpreted therefrom unless set out herein.

The acrylic polymer composition is generally present as a powder prior to mixing with the monomer composition. The powder component generally includes any filler prior to mixing with the monomer component so that the filler forms part of the dry powder polymer composition. The weight ratio of powder component to monomer component is generally <3:1, more preferably, <2.5:1, most preferably, <2.2:1. Typically, the weight ratio is in the range 2.15-1.85:1.

According to a further aspect of the present invention there is provided a method of producing an acrylic polymer composition comprising the steps of:—
(a) emulsion polymerizing an acrylic monomer composition to produce a polymer emulsion;
(b) drying the polymer emulsion of step (a) to produce acrylic polymer particles according to the first aspect of the present invention; and (c) optionally, mixing the acrylic polymer particles of step (b) with at least one further type of acrylic polymer particles and/or filler to produce an acrylic polymer composition suitable for hardening at a predetermined rate in the presence of an acrylic monomer composition.

Preferably, step (a) comprises seed, core and at least one shell emulsion polymerisation step. A particularly preferred method introduces an excess of initiator into the emulsion polymerization step (a) so that residual initiator is encapsulated within the emulsion particles. Preferably, in a multistage emulsion polymerization, the excess initator is introduced during the final stage so that it is present in the outer shell of the multistage particle. However, alternatively, initiator can also be added subsequently to the acrylic polymer composition.

Variation in the amount of encapsulated residual initiator or added initiator (e.g. dibenzoyl peroxide) has the effect of varying the set time of the hardenable composition. Increased initiator level results in shortened set time. Additionally, variation of the amount of accelerator (e.g. DMPT) in the acrylic monomer composition can also affect the set time. Increased accelerator concentration results in shortened set time.

An advantage of the acrylic polymer particles of the first aspect of the invention is the rapid dough time that is reached in the presence of the acrylic monomer composition. However, the working time and set time for the dough need to vary depending on the application. If a very short working time and set time are required then the acrylic polymer particles of the first aspect of the invention may be used alone. Nevertheless, in most applications, a longer working time and set time will be required and this can be achieved by varying the amount, type and particle size of the further type of acrylic polymer particle. Polymer particles of smaller average particle size (e.g. typically <20 microns) are known to also give short working times but by increasing the amount of particles of larger particle size and by increasing the particle size itself, longer working times can be achieved. Accordingly, the particle size and amount of further acrylic polymer particles depends upon the final application and this will be appreciated by the skilled person.

Typically, the further type of acrylic polymer particle is in the form of a solid polymer particle known as a polymer bead. Such beads, as mentioned above, are typically produced by suspension polymerisation although solution and bulk polymerization are also possible methods of production. Such beads may also contain encapsulated residual initiator as described for the emulsion polymerized microparticles above. Although the average particle size of such beads is variable as mentioned above, depending upon the final application, a typical average particle size for such beads is in the range 10-1000 microns, more typically, 20-250 microns, most typically, 25-125 microns. The larger the average particles size, the longer the working time. The skilled person will also appreciate that the molecular weight of the polymer and the presence of accelerators can also influence the working time and the set time. An important aspect of the present invention is therefore the reduced dough time achievable by the presence of the first type of acrylic polymer particles whereas the invention is not restricted to a particular working time or set time because this will depend on the application.

Notwithstanding the foregoing, a particularly advantageous application of the acrylic polymer composition of the aspects of the invention is its use in bone cement compositions. Such compositions are used in vertebroplasty and demand very short dough times so that the operation may proceed without undue delay. In addition, such uses demand short set times so that immobilization of the patient in the operating site is not unnecessarily prolonged. A competing requirement is sufficient working time to carry out the procedure effectively. Shortening the dough time has the effect of increasing the work time. A similar application for the compositions of the present invention is dental repairs where similar short doughing times are required.

Nevertheless, short dough times can be seen as generally desirable in many industrial applications and therefore, the invention is not restricted to bone cement and dental applications although these are preferred embodiments.

Accordingly, the invention extends to the use of acrylic polymer particles formed of a network of coalesced emulsion polymerized acrylic microparticles as a dough time reduction agent in a hardenable two part acrylic composition.

The ratio of the first type of acrylic polymer particles of the aspects of the invention to the total said further type of acrylic polymer particles varies depending on the final application. Nevertheless, it is advantageous in some applications such as bone cements to have a ratio thereof of between 2-45:98-55 w/w thereof, more preferably, 5-35:95-65 w/w, most preferably, 10-25:90-75 w/w. Such a ratio gives a good balance between short dough times and long work times. However, no restriction should be taken hereby and other higher emulsion polymerized microparticle ratios are also possible such as 100% w/w emulsion polymerized microparticles forming the polymer component of the first part or a ratio of 30-70:70-30, more typically, 40-60:60-40.

Emulsion polymerized particles are well known in the field of impact modifiers. For this reason an impact modifier such as butadiene or butyl acrylate is typically introduced as a comonomer into one of the shells of the multistage core shell particle. However, in the hardenable compositions of the present invention, an impact modifier may not be required. Accordingly, the emulsion microparticles of the present invention may be free from impact modifier co-monomer residues.

Although, the molecular weights of the polymers in the polymer powder component of the hardenable composition may influence the dough and work times, the invention is not restricted to any particular molecular weight. Nevertheless, the molecular weight (Mw) of the emulsion polymerized particles may be in the range 25,000-3,000,000, whereas the molecular weight of the further type of polymer particle may be in the range 25,000-2,000,000. In any case, reductions in the molecular weight and/or increases in the particle size of the further acrylic polymer particles can be used to increase the work time of the hardenable composition.

The acrylic polymer composition first part of the present invention may be provided separately as a dry powder either with or without added filler for later use as a hardenable composition. Accordingly, according to a still further aspect of the present invention there is provided a powder, preferably a dry powder, composition comprising a first type of acrylic polymer particles characterized in that each first type of acrylic polymer particle is formed of a network of coalesced emulsion polymerized acrylic microparticles, and optionally, at least one further type of acrylic polymer particles blended therewith.

Preferably, the emulsion particles of the powder composition incorporate a suitable initiator compound in their polymer matrix, in the case of multistage emulsion particles, the initiator is incorporated in their outer shell in the final stage.

Embodiments of the invention will now be described with reference to the accompanying examples and by reference to the drawings in which:—

FIG. 1a shows an SEM view of the surface of a spray dried polymer particle according to the invention;

FIG. 1b shows a further SEM view of the same type of particle as FIG. 1a;

FIG. 2a shows an SEM view of the surface of a coagulated and dried polymer particle according to the invention; and FIG. 2b shows a further SEM view of the same type of particle as FIG. 2a.

EXAMPLES

Use of emulsion polymerization and spray drying to produce PMMA with a significant proportion of PMMA particles being formed from coalesced emulsion polymerized microparticles.

Example 1

Emulsion Polymerisation 1.0 liter of deionised water is added to a five-liter round bottomed glass flask fitted with a nitrogen inlet, condenser and electrically operated stainless steel paddle stirrer. The water is heated to 82° C. by means of an electric heating mantle whilst stirring at 392 min$^{-1}$. A flow of nitrogen is passed through the vapour space of the flask above the surface of the liquid.

A monomer mixture is prepared consisting of 500 grams methyl methacrylate (containing 5 ppm of Topanol A inhibitor) and 5.0 grams of 75% active sodium dioctylsulphosuccinate emulsifier (trade name: Aerosol™ OT). These components are mixed before use.

With the temperature of the water at 82° C., a polymer seed (Stage 1) is prepared by adding 50 grams of the monomer mixture to the flask followed by 10 milliliters of a 2 wt % solution of potassium persulphate in deionised water. Following a slight exotherm, the reaction proceeds for thirty minutes until the temperature returns to 82° C.

The core is then grown over the polymer seed particles (Stage 2) by firstly adding 20 milliliters of a 2 wt % solution of potassium persulphate in deionised water to the flask followed by continuous addition of 350 grams of the monomer mixture over approximately 35 minutes using a peristaltic pump. The reaction proceeds for a further fifteen minutes after the completion of the monomer mixture addition until the temperature returns to 82° C.

7.0 grams of 70% active dibenzoyl peroxide are dissolved in the remaining 100 grams of monomer mixture at room temperature of 20-23° C. immediately before use. This produces a residual dibenzoyl peroxide (BPO) content of approximately 1 wt % in the polymer.

The BPO-containing shell is then grown over the core (Stage 3) by firstly adding five milliliters of a 2 wt % solution of potassium persulphate in deionised water to the flask followed by continuous addition of the monomer mixture containing added BPO over approximately 10 minutes using a peristaltic pump. The reaction proceeds for a further fifteen minutes after all the monomer mixture has been added until the temperature has returned to 82° C.

The resultant emulsion is then cooled to below 40° C. and filtered through a 150 micron screen.

The Z average emulsion particle size was determined using a Malvern Zetasizer nano series S particle size analyzer.

Spray Drying

The emulsion is isolated as a powder by spray drying using a LabPlant™ SD05 laboratory spray dryer. The inlet temperature was 135° C., the latex feed rate was set at 15, a 1.0 mm jet size was employed and the maximum settings for air flow rate and air compressor pressure were used.

The resultant powder was characterised: for particle size (d10, d50, d90) as measured by a Malvern Mastersizer 2000 particle size analyzer; for the proportion of the spray dried powder that has particle size <20 microns and <10 microns by Malvern Mastersizer 2000; for wt % moisture content by Karl Fischer titration; for reduced viscosity (RV) (dl/g) in chloroform (1 wt % solution); for molecular weight by gel permeation chromatography (GPC); and for wt % residual dibenzoyl peroxide content by titration.

d10, d50, d90 are standard "percentile" readings from the particle size analysis.

d50 is the size in microns at which 50% of the sample is smaller and 50% is larger.

d10 is the size of particle below which 10% of the sample lies.

d90 is the size of particle below which 90% of the sample lies.

The characterisation results are tabulated in table 1.

Example 2

As example 1 but with 14.0 grams of 70% active dibenzoyl peroxide and stirrer speed reduced to 300 min$^{-1}$.

Example 3

As example 2, but with the addition of approximately 1.0 gram of 1-dodecanethiol to the initial monomer mixture prior to commencing the polymerisation to cause a reduction in polymer molecular weight.

Example 4

As example 3, but increasing the 1-dodecanethiol content to 2.0 grams to further reduce the polymer molecular weight.

Example 5

As example 4, but with 21.0 grams of 70% active dibenzoyl peroxide in Stage 3.

Example 6

As example 3, but batch size doubled and reaction temperature reduced to 80° C.

Example 7

As example 6, but 1-dodecanethiol content reduced from 2.0 grams to 1.85 grams to increase the polymer molecular weight, and the amount of 70% active dibenzoyl peroxide added in Stage 3 increased from 28 grams to 30 grams to increase the amount of residual dibenzoyl peroxide in the resultant emulsion polymerized microparticles.

Example 8

Emulsion Polymerisation

Using Emulsified Monomer Feed 1.5 liters of deionised water is added to a five-liter round bottomed glass flask fitted with a nitrogen inlet, condenser The Z average emulsion particle size was determined using a Malvern Zetasizer nano series S particle size analyzer and the emulsion was spray dried using the same method as example 1.

Example 9

As example 8, but run at 300 min$^{-1}$ stirrer speed and the emulsified monomer mixture was added over 90 minutes during Stage 2.

TABLE 1

| example | 1 | 2 | 3 | 4 | 5 | 6 | 7 | 8 | 9 |
|---|---|---|---|---|---|---|---|---|---|
| emulsion Z-average particle size nm | 179 | 207 | 197 | 195 | 205 | 215 | 215 | 202 | 211 |
| Powder d10 μm | not measured | not measured | not measured | not measured | not measured | 9.5 | 8.6 | 6.8 | 9.4 |
| Powder d50 μm | not measured | not measured | not measured | not measured | not measured | 27.4 | 25.9 | 15.7 | 24.9 |
| Powder d90 μm | not measured | not measured | not measured | not measured | not measured | 71.6 | 62.9 | 32.1 | 56.7 |
| RV dl/g | 2.89 | 3.00 | 2.00 | 0.96 | 1.03 | 1.97 | 2.09 | 1.03 | 1.13 |
| residual BPO wt % | 1.00 | 2.10 | 1.90 | 1.77 | 2.63 | 1.80 | 2.02 | 1.81 | 1.93 |
| Mw (Daltons) | not measured | not measured | not measured | 155,250 | 168,650 | 323,200 | 339,450 | 164,850 | 200,900 |
| Mn (Daltons) | not measured | not measured | not measured | 71,325 | 72,825 | 139,225 | 151,800 | 79,225 | 88,850 |
| d | not measured | not measured | not measured | 2.18 | 2.32 | 2.32 | 2.24 | 2.08 | 2.26 | and electrically operated stainless steel paddle stirrer. The water is heated to 80° C. by means of an electric heating mantle whilst stirring at 390 min$^{-1}$. A flow of nitrogen is passed through the vapour space of the flask above the surface of the liquid.

An emulsified monomer mixture is prepared consisting of 1000 grams methyl methacrylate (containing 5 ppm of Topanol A inhibitor), 1.85 grams of 1-dodecanethiol, 10.0 grams of 75% sodium dioctylsulphosuccinate emulsifier (trade name: Aerosol™ OT) and 0.5 liter deionised water. This mixture is stirred prior to and throughout addition to keep it emulsified.

With the temperature of the water at 80° C., a polymer seed (Stage 1) is prepared by adding 162.5 grams of the monomer mixture to the flask followed by 10 milliliters of a 2 wt % solution of potassium persulphate in deionised water. Following a slight exotherm, the reaction proceeds for thirty minutes until the temperature returns to 80° C.

The core is then grown over the polymer seed particles (Stage 2) by firstly adding 20 milliliters of a 2 wt % solution of potassium persulphate in deionised water to the flask followed by continuous addition of 1147.5 grams of the emulsified monomer mixture over approximately 135 minutes using a peristaltic pump. The reaction proceeds for a further fifteen minutes after the completion of the monomer mixture until the temperature returns to 80° C.

30.0 grams of 70% active dibenzoyl peroxide are dissolved in the remaining 200 grams of emulsified monomer mixture at room temperature of 20-23° C. immediately before use.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 24 minutes using a peristaltic pump. The reaction proceeds for a further fifteen minutes after all the monomer mixture has been added until the temperature has returned to 80° C.

The resultant emulsion is then cooled to below 40° C. and filtered through a 150 micron screen.

Example 10

A batch of emulsion was prepared according to example 6 and recovered as a powder using a coagulation approach, rather than spray drying, as follows:

A solution of 100 grams of magnesium sulphate heptahydrate in 2 liters of deionised water was heated to 80° C. with stirring at 600 rpm. 1000 g of emulsion as prepared in example 6 was added to the solution using a peristaltic pump with flow rate of approximately 33 grams per minute. The resulting mixture was held for five minutes after the end of the addition before cooling to 40° C. The polymer was then filtered, washing with deionised water and dried in an oven at 60° C. until dry.

The polymer had a particle size (d50) of 183 μm and a molecular weight (Mw) of approximately 476,000 Daltons.

Example 11

This example describes the blending of spray dried emulsion polymer with conventional PMMA beads.

A general lab scale method of blending spray dried PMMA powder with conventional PMMA beads is to use a tumble blending approach in a suitable container. The container is typically filled to three quarters of the total volume and the blending time is typically 15 to 30 minutes.

The starting PMMA bead polymer (Colacryl®B866, obtained from Lucite International Speciality Polymers & Resins Limited) has a RV of 2.4 dl/g, Mw 421,200, residual BPO 2.94% wt, mean particle size 39 microns and d50 of 44 microns. This was blended with spray dried PMMA powder prepared according to the method of example 7 in varying proportions.

The blends were then mixed with MMA monomer containing 60 ppm HQ inhibitor at 20° C. in the ratio 20 g polymer to 10 ml monomer and the dough and work times were measured. Before mixing the two components were equilibrated in an incubator at 20 deg C. for at least 10 hours. The required amount of polymer was then placed into a polypropylene beaker, followed by the monomer. Timing was started from the point of adding the powder to the liquid. Hand mixing was then carried out for 30 seconds using a metal spatula, whereupon the material was covered and left to stand. Periodically, the material was assessed for consistency and the dough and work time determined. Table 2 records the results.

TABLE 2

| PMMA bead polymer % wt | PMMA spray dried emulsion powder % wt | Dough time mins:secs | Work time mins:secs |
|---|---|---|---|
| 100 | 0 | 21:00 | 32:00 |
| 90 | 10 | 8:00 | 30:00 |
| 85 | 15 | 2:30 | 28:00 |
| 80 | 20 | 1:00 | 22:00 |
| 75 | 25 | 0:40 | 18:00 |
| 60 | 40 | 0:25 | 3:00 |

Table 2 shows how increasing the amount of spray dried emulsion powder in the blend significantly shortens the dough time. Moreover, the fast dough times can be achieved without appreciable reduction in the work time.

Example 12

Example 11 was repeated, except that the liquid component was MMA containing 60 ppm HQ inhibitor and 1% DMPT accelerator. Table 3 records the results.

TABLE 3

| PMMA bead polymer % wt | PMMA spray dried emulsion powder % wt | Dough time mins:secs | Work time mins:secs | Set time mins:secs |
|---|---|---|---|---|
| 100 | 0 | 21:00 | 14:00 | 37:00 |
| 90 | 10 | 8:00 | 17:00 | 30:00 |
| 85 | 15 | 2:40 | 20:00 | 24:00 |
| 80 | 20 | 1:10 | 14:00 | 20:00 |
| 75 | 25 | 0:40 | 10:00 | 17:00 |
| 60 | 40 | 0:25 | 2:00 | 11:00 |

Comparison of table 3 with table 2 shows that the addition of DMPT accelerator to the liquid significantly shortens the work time, but has no appreciable effect on the dough time.

Example 13

This example compares the handling properties of polymer blends prepared with emulsion polymer recovered as a powder by different processes (spray drying and coagulation). Also, as comparative examples, the handling properties of a sieved PMMA bead polymer and a ball milled PMMA polymer are also shown.

PMMA emulsion was recovered as a powder in different ways, i.e., (i) spray dried emulsion polymer according to the method of example 1 and (ii) coagulated emulsion prepared according to the method of example 10. The PMMA dried emulsion powders (i) and (ii) were then blended with PMMA beads in the ratio 15% wt of PMMA dried emulsion powder and 85% wt of PMMA beads. The PMMA bead polymer was Colacryl®B866, obtained from Lucite International Speciality Polymers & Resins Limited. This has an RV of 2.4 dl/g, Mw 421,200, residual BPO 2.94% wt, mean particle size 39 microns and d50 of 44 microns.

Two comparative examples were prepared, i.e., (iii) sieving of PMMA bead polymer (RV 2.1) (Colacryl®TS1890, obtained from Lucite International Speciality Polymers & Resins Limited) through a 38 micron mesh screen and retaining the powder that passed through the screen. The resultant fractionated powder was then used without further treatment. This had mean particle size 15 microns and d50 of 15 microns. The amount of particles <20 microns was 70.6%. The other comparative example, (iv), was prepared by ball-milling PMMA bead polymer (Colacryl®B866, obtained from Lucite International Speciality Polymers & Resins Limited) for 28 hours. This sample was used direct from the ball mill without further treatment.

A Control sample, Colacryl®B866, obtained from Lucite International Speciality Polymers & Resins Limited, was also selected for testing as the sole powder component. This sample, along with samples (i) to (iv) were then mixed with MMA monomer containing 60 ppm HQ at 20° C. in the ratio 20 g polymer to 10 ml monomer and the dough and work times were measured. Before mixing, all materials were equilibrated in an incubator at 20° C. for at least 10 hours. The required amount of polymer was then placed into a polypropylene beaker, followed by the monomer. Timing was started from the point of adding the powder to the liquid. Hand mixing was then carried out for 30 seconds using a metal spatula, whereupon the material was covered and left to stand. Periodically, the material was assessed for consistency and the dough, work and set times determined. Table 4 records the results.

TABLE 4

| Method of PMMA powder preparation | PMMA powder type | Dough time, mins:secs | Work time, mins |
|---|---|---|---|
| (i) | spray dried emulsion | 2:50 | 30 |
| (ii) | coagulated emulsion | 2:55 | 30 |
| (iii) Comparative Example | Sieved PMMA, | 7:00 | 18 |
| (iv) Comparative Example | Ball-milled PMMA | 2:30 | 8 |
| Control | PMMA bead only (Colacryl ® B866) (no added PMMA emulsion powder) | 21:00 | 32 |

Table 4 shows that both PMMA powders that contained emulsion microparticles (i) and (ii) have similar dough times, regardless of how they have been prepared. Additionally, they still retain the relatively long work time of the Control sample. This contrasts with comparative example (iii) that has a high fraction of <20 micron particles isolated by a sieving process. In this case, increasing the amount of particles <20 microns provides a modest reduction in dough time, but this has the additional disadvantage of having a shortened work time. The performance of samples (i) and (ii) also contrasts with the ball-milled PMMA, (comparative example (iv)), which has similar fast doughing characteristics to the powders incorporating the emulsion polymer. However, sample (iv) has the disadvantage of having a much reduced work time.

Example 14

This example shows the effect of residual peroxide level in spray dried PMMA emulsion powder on handling properties.

The PMMA bead polymer, Colacryl®B866, obtained from Lucite International Speciality Polymers & Resins Limited, has an RV of 2.4 dl/g, Mw 421,200, residual BPO 2.94% wt, mean particle size 39 microns and d50 of 44 microns.

All the polymer blends comprised 85% wt of PMMA bead and 15% wt of spray dried PMMA powders varying in the amount of dibenzoyl peroxide containing in the shell of the PMMA emulsion. The blends were then mixed with MMA monomer containing 60 ppm HQ inhibitor and 1% DMPT accelerator at 20° C. in the ratio 20 g polymer to 10 ml monomer and the dough and work times were measured. Before mixing the two components were equilibrated in an incubator at 20° C. for at least 10 hours. The required amount of polymer was then placed into a polypropylene beaker, followed by the monomer. Timing was started from the point of adding the powder to the liquid. Hand mixing was then carried out for 30 seconds using a metal spatula, whereupon the material was covered and left to stand. Periodically, the material was assessed for consistency and the dough, work and set times determined. Table 5 records the results.

TABLE 5

| Residual BPO in spray dried PMMA powder (% wt) | Dough time, mins:secs | Work time, mins | Set time, mins |
| --- | --- | --- | --- |
| 0 | 2:10 | 28 | 45 |
| 1.1 | 2:00 | 24 | 33 |
| 1.65 | 2:00 | 24 | 29 |
| 1.9 | 2:00 | 22 | 27 |
| 2.1 | 2:10 | 20 | 24 |
| Control (no added PMMA powder) Colacryl ® B866 only | 21:00 | 31 | 40 |

Table 5 shows that the amount of residual BPO has little effect on the dough time, but increasing amounts lead to shorter set and work times.

Example 15

Reduced viscosity (RV) is a convenient measure of molecular weight. This example shows the effect of RV of the spray dried PMMA emulsion powder on handling properties.

The PMMA bead polymer, Colacryl®B866, obtained from Lucite International Speciality Polymers & Resins Limited, has an RV of 2.4 dl/g, Mw 421,200, residual BPO 2.94% wt, mean particle size 39 microns and d50 of 44 microns.

All the polymer blends comprised 85% wt of PMMA bead and 15% wt of spray dried PMMA powders. The blends were then mixed with MMA monomer containing 60 ppm HQ inhibitor at 20° C. in the ratio 20 g polymer to 10 ml monomer and the dough and work times were measured. Before mixing the two components were equilibrated in an incubator at 20° C. for at least 10 hours. The required amount of monomer was then placed into a polypropylene beaker, followed by the polymer powder. Timing was started from the point of adding the powder to the liquid. Hand mixing was then carried out for 30 seconds using a metal spatula, whereupon the material was covered and left to stand. Periodically, the material was assessed for consistency and the dough, work and set times determined. Table 6 records the results.

TABLE 6

| RV of spray dried PMMA powder (dl/g) | Dough time mins:secs | Work time mins:secs |
| --- | --- | --- |
| Control (no added PMMA powder) Colacryl ® B866 only | 22 | 32 |
| 1.0 | 10 | 24 |
| 2.0 | 2:50 | 28 |
| 2.6 | 2:40 | 25 |
| 3.0 | 2:30 | 24 |

Table 6 shows that higher RV (higher molecular weight) favours shorter dough times.

Example 16

Example 15 was repeated, except that the liquid component was MMA containing 60 ppm HQ inhibitor and 1% DMPT accelerator. Table 7 records the results.

TABLE 7

| RV of spray dried PMMA powder (dl/g) | Dough time mins:secs | Work time mins:secs | Set time Mins:secs |
| --- | --- | --- | --- |
| Control (no added PMMA powder) Colacryl ® B866 only | 21 | 14 | 37 |
| 1.0 | 9 | 9 | 24 |
| 2.0 | 2:50 | 19 | 22 |
| 2.6 | 2:30 | 19 | 24 |
| 3.0 | 2:20 | 18 | 23 |

Comparison of table 7 with table 6 shows that the addition of DMPT accelerator to the liquid significantly shortens the work time, but has no appreciable effect on the dough time.

Example 17

This example shows the effect of DMPT accelerator on handling properties.

The PMMA bead polymer, Colacryl®B866, obtained from Lucite International Speciality Polymers & Resins Limited, had RV 2.4 dl/g, Mw 421,200, residual BPO 2.94% wt, mean particle size 39 microns and d50 of 44 microns.

The spray dried PMMA powder had RV 2.4 dl/g and residual BPO 1.98% wt and was made following the procedural steps of example 7 with the amount of 1-dodecanethiol with respect to total monomer in the monomer mix reduced to 0.0867% w/w from 0.185 w/w to achieve the higher RV. All the subsequent polymer blends comprised 85% wt of PMMA bead and 15% wt of spray dried PMMA powder.

The MMA monomer contained 60 ppm HQ inhibitor and amounts of DMPT accelerator varying from 0.25% wt to 1.5% wt.

The blends were mixed with the monomer at 20° C. in the ratio 20 g polymer to 10 ml monomer and the dough, work and set times were measured. Before mixing, the two components were equilibrated in an incubator at 20° C. for at least 10 hours. The required amount of monomer was then placed into a polypropylene beaker, followed by the polymer powder. Timing was started from the point of adding the powder to the liquid. Hand mixing was then carried out for 30 seconds using a metal spatula, whereupon the material was covered and left to stand. Periodically, the material was assessed for consistency and the dough, work and set times determined. Table 8 records the results.

TABLE 8

| % wt of DMPT | Dough time mins:secs | Work time mins:secs | Set time Mins:secs |
| --- | --- | --- | --- |
| 0.25 | 2:30 | 38 | 55 |
| 0.5 | 2:30 | 21 | 28 |
| 0.75 | 2:30 | 20 | 25 |
| 1.0 | 2:30 | 18 | 24 |
| 1.5 | 2:30 | 14 | 19 |

Table 8 shows that the amount of DMPT accelerator has little effect on the dough time, but increasing amounts lead to shorter work and set times.

Examples 18 and 19 demonstrate how the Z-average particle size of the emulsion polymerized microparticles can be varied.

Example 18

This example shows that a relatively large Z-average particle size in the emulsion polymerized microparticles can be achieved by reducing the amount of sodium dioctylsulphosuccinate emulsifier (trade name: Aerosol™ OT) employed.

2.0 liters of deionised water is added to a five-liter round bottomed glass flask fitted with nitrogen tube, condenser and electrically operated stainless steel paddle stirrer. The water is heated to 80° C. by means of an electronically controlled electric heating mantle whilst being stirred at 300 min$^{-1}$. A flow of nitrogen is passed through the vapour space of the flask above the surface of the liquid.

A monomer mixture is prepared consisting of 1000 grams methyl methacrylate (containing 5 ppm of Topanol A inhibitor), 1.85 grams of 1-dodecanethiol and 1.34 grams of 75% active Aerosol™ OT.

When the temperature of the water has settled at 80° C., a polymer seed (Stage 1) is prepared by adding 100 grams of the monomer mixture to the flask followed by 10 milliliters of a 2 wt % solution of potassium persulphate in deionised water. The resultant polymerization exotherm is allowed to subside (approximately 30 minutes) and the temperature of the reactor contents return to 80° C.

The polymer core is then grown over the polymer seed particles (Stage 2) by firstly adding 20 milliliters of a 2 wt % solution of potassium persulphate in deionised water to the flask followed by continuous addition of 700 grams of the monomer mixture over approximately 75 minutes using a peristaltic pump. The reaction is allowed to proceed for a further fifteen minutes after completing the monomer mixture addition with temperature set at 80° C.

28.0 grams of 75% active dibenzoyl peroxide (BPO) are dissolved in the remaining 200 grams of monomer mixture at room temperature of 20-23° C. immediately before use.

The BPO-containing shell is then grown over the core (Stage 3) by firstly adding 10 milliliters of the 2 wt % solution of potassium persulphate in deionised water to the flask followed by continuous addition of the remaining monomer mixture containing added BPO over approximately 25 minutes using a peristaltic pump. The reaction is allowed to proceed for a further fifteen minutes after completing the monomer mixture addition with temperature set at 80° C.

The resultant emulsion is then cooled to below 40° C. and filtered through a 150 micron screen. The Z-average particle size for the resultant emulsion is determined using a Malvern Zetasizer nano series S particle size analyzer and found to be 437 nm.

The emulsion is isolated as a powder by spray drying using the method of example 1 and characterized for particle size (d10, d50, d90) as measured by a Malvern Mastersizer 2000 particle size analyzer; for reduced viscosity (RV) (dl/g) in chloroform (1 wt % solution); for molecular weight by gel permeation chromatography (GPC); and for wt % residual dibenzoyl peroxide content by titration.

d10, d50, d90 are standard "percentile" readings from the particle size analysis.

d50 is the size in microns at which 50% of the sample is smaller and 50% is larger.

d10 is the size of particle below which 10% of the sample lies.

d90 is the size of particle below which 90% of the sample lies

The characterization results are tabulated in table 10.

Example 19

This example shows that a relatively small Z-average particle size can be achieved by increasing the amount of monomer used to make the seed (Stage 1) and reducing the amount of monomer used to form the core (Stage 2).

2.0 liters of deionised water is added to a five-liter round bottomed glass flask fitted with nitrogen tube, condenser and electrically operated stainless steel paddle stirrer. The water is heated to 80° C. by means of an electronically controlled electric heating mantle whilst being stirred at 300 min$^{-1}$. A flow of nitrogen is passed through the vapour space of the flask above the surface of the liquid.

A monomer mixture is prepared consisting of 1000 grams methyl methacrylate (containing 5 ppm of Topanol A inhibitor), 1.85 grams of 1-dodecanethiol and 10.0 grams of 75% active Aerosol™ OT.

When the temperature of the water has settled at 80° C., a polymer seed (Stage 1) is prepared by adding 250 grams of the monomer mixture to the flask followed by 20 milliliters of a 2 wt % solution of potassium persulphate in deionised water. The resultant polymerization exotherm is allowed to subside (approximately 30 minutes) and the temperature of the reactor contents return to 80° C.

The polymer core is then grown over the polymer seed particles (Stage 2) by firstly adding 15 milliliters of a 2 wt % solution of potassium persulphate in deionised water to the flask followed by continuous addition of 550 grams of the monomer mixture over approximately 60 minutes using a peristaltic pump. The reaction is allowed to proceed for a further fifteen minutes after completing the monomer mixture addition with temperature set at 80° C.

28.0 grams of 75% active dibenzoyl peroxide (BPO) are dissolved in the remaining 200 grams of monomer mixture at room temperature of 20-23° C. immediately before use.

The BPO-containing shell is then grown over the core (Stage 3) by firstly adding 10 milliliters of the 2 wt % solution of potassium persulphate in deionised water to the flask followed by continuous addition of the remaining monomer mixture containing added BPO over approximately 25 minutes using a peristaltic pump. The reaction is allowed to proceed for a further fifteen minutes after completing the monomer mixture addition with temperature set at 80° C.

The resultant emulsion is then cooled to below 40° C. and filtered through a 150 micron screen.

The Z-average particle size for the resultant emulsion was 165 nm (see table 10).

The emulsion is isolated as a powder by spray drying using the method of example 1 and characterized as per example 18. The characterization results are tabulated in table 10.

Examples 20-23 demonstrate how the level of initiator remaining in the emulsion polymerized microparticles can be varied.

Example 20

2.0 liters of deionised water is added to a five-liter round bottomed glass flask fitted with nitrogen tube, condenser and electrically operated stainless steel paddle stirrer. The water is heated to 80° C. by means of an electronically controlled electric heating mantle whilst being stirred at 300 min$^{-1}$. A flow of nitrogen is passed through the vapour space of the flask above the surface of the liquid.

A monomer mixture is prepared consisting of 1000 grams methyl methacrylate (containing 5 ppm of Topanol A inhibitor), 1.85 grams of 1-dodecanethiol and 10.0 grams of 75% active Aerosol™ OT.

When the temperature of the water has settled at 80° C., a polymer seed (Stage 1) is prepared by adding 100 grams of the monomer mixture to the flask followed by 10 milliliters of a 2 wt % solution of potassium persulphate in deionised water. The resultant polymerization exotherm is allowed to subside (approximately 30 minutes) and the temperature of the reactor contents return to 80° C.

The polymer core is then grown over the polymer seed particles (Stage 2) by firstly adding 15 milliliters of a 2 wt % solution of potassium persulphate in deionised water to the flask followed by continuous addition of 600 grams of the monomer mixture over approximately 65 minutes using a peristaltic pump. The reaction is allowed to proceed for a further fifteen minutes after completing the monomer mixture addition with temperature set at 80° C.

42.0 grams of 75% active dibenzoyl peroxide (BPO) are dissolved in the remaining 300 grams of monomer mixture at room temperature of 20-23° C. immediately before use.

After the reactor contents have returned to 80° C., the BPO-containing shell is then grown over the core (Stage 3) by firstly adding 15 milliliters of the 2 wt % solution of potassium persulphate in deionised water to the flask followed by continuous addition of the remaining monomer mixture containing added BPO over approximately 30 minutes using a peristaltic pump. The reaction is allowed to proceed for a further fifteen minutes after completing the monomer mixture addition with temperature set at 80° C.

The resultant emulsion is then cooled to below 40° C. and filtered through a 150 micron screen.

The emulsion is isolated as a powder by spray drying using the method of example 1 and characterized as per example 18. The characterization results are tabulated in table 10.

The amount of BPO initiator remaining in the emulsion polymerized microparticles was measured to be 2.30 wt %.

Example 21

Example 20 was repeated, except for using a greater amount of 75% active dibenzoyl peroxide (BPO) during Stage 3, i.e. 49.0 grams.

The amount of BPO initiator remaining in the emulsion polymerized microparticles was measured to be 2.50 wt % (see table 10).

Example 22

2.0 liters of deionised water is added to a five-liter round bottomed glass flask fitted with nitrogen tube, condenser and electrically operated stainless steel paddle stirrer. The water is heated to 80° C. by means of an electronically controlled electric heating mantle whilst being stirred at 300 min$^{-1}$. A flow of nitrogen is passed through the vapour space of the flask above the surface of the liquid.

A monomer mixture is prepared consisting of 1000 grams methyl methacrylate (containing 5 ppm of Topanol A inhibitor), 1.85 grams of 1-dodecanethiol and 10.0 grams of 75% active Aerosol™ OT.

When the temperature of the water has settled at 80° C., a polymer seed (Stage 1) is prepared by adding 100 grams of the monomer mixture to the flask followed by 10 milliliters of a 2 wt % solution of potassium persulphate in deionised water. The resultant polymerization exotherm is allowed to subside (approximately 30 minutes) and the temperature of the reactor contents return to 80° C.

The polymer core is then grown over the polymer seed particles (Stage 2) by firstly adding 15 milliliters of a 2 wt % solution of potassium persulphate in deionised water to the flask followed by continuous addition of 500 grams of the monomer mixture over approximately 55 minutes using a peristaltic pump. The reaction is allowed to proceed for a further fifteen minutes after completing the monomer mixture addition with temperature set at 80° C.

67.0 grams of 75% active dibenzoyl peroxide (BPO) are dissolved in the remaining 400 grams of monomer mixture at room temperature of 20-23° C. immediately before use.

After the reactor contents have returned to 80° C., the BPO-containing shell is then grown over the core (Stage 3) by firstly adding 15 milliliters of the 2 wt % solution of potassium persulphate in deionised water to the flask followed by continuous addition of the remaining monomer mixture containing added BPO over approximately 30 minutes using a peristaltic pump. The reaction is allowed to proceed for a further fifteen minutes after completing the monomer mixture addition with temperature set at 80° C.

The resultant emulsion is then cooled to below 40° C. and filtered through a 150 micron screen.

The emulsion is isolated as a powder by spray drying using the method of example 1 and characterized as per example 18. The characterisation results are tabulated in table 10.

The amount of BPO initiator remaining in the emulsion polymerized microparticles was measured to be 3.05 wt %.

Example 23

2.0 liters of deionised water is added to a five-liter round bottomed glass flask fitted with nitrogen tube, condenser and electrically operated stainless steel paddle stirrer. The water is heated to 80° C. by means of an electronically controlled electric heating mantle whilst being stirred at 300 min$^{-1}$. A flow of nitrogen is passed through the vapour space of the flask above the surface of the liquid.

A monomer mixture is prepared consisting of 1000 grams methyl methacrylate (containing 5 ppm of Topanol A inhibitor), 1.85 grams of 1-dodecanethiol and 10.0 grams of 75% active Aerosol™ OT.

When the temperature of the water has settled at 80° C., a polymer seed (Stage 1) is prepared by adding 50 grams of the monomer mixture to the flask followed by 10 milliliters of a 2 wt % solution of potassium persulphate in deionised water. The resultant polymerization exotherm is allowed to subside (approximately 30 minutes) and the temperature of the reactor contents return to 80° C.

The polymer core is then grown over the polymer seed particles (Stage 2) by firstly adding 15 milliliters of a 2 wt % solution of potassium persulphate in deionised water to the flask followed by continuous addition of 450 grams of the monomer mixture over approximately 45 minutes using a peristaltic pump. The reaction is allowed to proceed for a further fifteen minutes after completing the monomer mixture addition with temperature set at 80° C.

100.0 grams of 75% active dibenzoyl peroxide (BPO) are dissolved in the remaining 500 grams of monomer mixture at room temperature of 20-23° C. immediately before use.

After the reactor contents have returned to 80° C., the BPO-containing shell is then grown over the core (Stage 3) by firstly adding 15 milliliters of the 2 wt % solution of potassium persulphate in deionised water to the flask followed by continuous addition of the remaining monomer mixture containing added BPO over approximately 30 minutes using a peristaltic pump. The reaction is allowed to proceed for a further fifteen minutes after completing the monomer mixture addition with temperature set at 80° C.

The resultant emulsion is then cooled to below 40° C. and filtered through a 150 micron screen.

The emulsion is isolated as a powder by spray drying using the method of example 1 and characterized as per example 18. The characterisation results are tabulated in table 10.

The amount of BPO initiator remaining in the emulsion polymerized microparticles was measured to be 4.50 wt %.

Example 24

This example shows the effect of residual peroxide level in spray dried PMMA emulsion powder on handling properties and extends the range shown in example 14.

The PMMA bead polymer, Colacryl®B866, obtained from Lucite International Speciality Polymers & Resins Limited, has an RV of 2.4 dl/g, Mw 421,200, residual BPO 2.94% wt, mean particle size 39 microns and d50 of 44 microns.

All the polymer blends comprised 85% wt of PMMA bead and 15% wt of spray dried PMMA powders varying in the amount of dibenzoyl peroxide containing in the shell of the PMMA emulsion. The blends were then mixed with MMA monomer containing 60 ppm HQ inhibitor and 1% DMPT accelerator at 20° C. in the ratio 20 g polymer to 10 ml monomer and the dough and work times were measured. Before mixing the two components were equilibrated in an incubator at 20° C. for at least 10 hours. The required amount of polymer was then placed into a polypropylene beaker, followed by the monomer. Timing was started from the point of adding the powder to the liquid. Hand mixing was then carried out for 30 seconds using a metal spatula, whereupon the material was covered and left to stand. Periodically, the material was assessed for consistency and the dough, work and set times determined. Table 9 records the results.

TABLE 9

| Residual BPO in spray dried PMMA powder (% wt) | Dough time, mins:secs | Work time, mins | Set time, mins |
|---|---|---|---|
| 2.30 | 2:50 | 17 | 23 |
| 2.50 | 2:50 | 15 | 22 |
| 4.50 | 2:40 | 10 | 16 |

Table 9 shows that the amount of residual BPO has little effect on the dough time, but increasing amounts lead to shorter set and work times.

Example 25

This example demonstrates the preparation of the emulsion polymerized microparticles in two stages, rather than the three stages of the previous examples. Seed particles are initially formed which then act as nuclei for growing a combined core and shell.

2.0 liters of deionised water is added to a five-liter round bottomed glass flask fitted with nitrogen tube, condenser and electrically operated stainless steel paddle stirrer. The water is heated to 80° C. by means of an electronically controlled electric heating mantle whilst being stirred at 300 $min^{-1}$. A flow of nitrogen is passed through the vapour space of the flask above the surface of the liquid.

A monomer mixture is prepared consisting of 1000 grams methyl methacrylate (containing 5 ppm of Topanol A inhibitor), 1.85 grams of 1-dodecanethiol and 10.0 grams of 75% active Aerosol™ OT.

When the temperature of the water has settled at 80° C., a polymer seed (Stage 1) is prepared by adding 100 grams of the monomer mixture to the flask followed by 10 milliliters of a 2 wt % solution of potassium persulphate in deionised water. The resultant polymerization exotherm is allowed to subside (approximately 30 minutes) and the temperature of the reactor contents return to 80° C.

49.0 grams of 75% active dibenzoyl peroxide (BPO) are dissolved in the remaining 900 grams of monomer mixture at room temperature of 20-23° C. immediately before use.

The polymer core and shell is then grown over the polymer seed particles (Stage 2) by firstly adding 30 milliliters of a 2 wt % solution of potassium persulphate in deionised water to the flask followed by continuous addition of the remaining monomer mixture containing added BPO over approximately 90 minutes using a peristaltic pump. The reaction is allowed to proceed for a further fifteen minutes after completing the monomer mixture addition with temperature set at 80° C.

The resultant emulsion is then cooled to below 40° C. and filtered through a 150 micron screen. The Z-average particle size for the resultant emulsion was 206 nm.

The emulsion is isolated as a powder by spray drying using the method of example 1 and characterized as per example 18. The characterisation results are tabulated in table 10.

The amount of BPO initiator remaining in the emulsion polymerized microparticles was measured to be 2.80 wt %.

TABLE 10

| Example | 18 | 19 | 20 | 21 | 22 | 23 | 25 |
|---|---|---|---|---|---|---|---|
| emulsion Z-average particle size nm | 437 | 165 | 222 | 209 | 215 | 262 | 206 |
| Powder d10 μm | 8.4 | 11.7 | 6.2 | 6.5 | 5.9 | 5.6 | 8.0 |
| Powder d50 μm | 21.5 | 32.6 | 15.1 | 15.3 | 15.8 | 14.9 | 20.3 |
| Powder d90 μm | 44.0 | 66.2 | 32.8 | 31.8 | 34.0 | 32.4 | 42.3 |
| RV dl/g | not measured | not measured | 1.80 | 1.80 | 2.10 | 1.92 | 2.80 |
| residual BPO wt % | not measured | not measured | 2.30 | 2.50 | 3.05 | 4.50 | 2.80 |
| Mw (Daltons) | 552,275 | 396,000 | 341,825 | 408,350 | 467,725 | 450,650 | 438,350 |
| Mn (Daltons) | 225,150 | 142,625 | 157,700 | 188,300 | 216,875 | 201,450 | 211,550 |
| d | 2.45 | 2.78 | 2.17 | 2.17 | 2.16 | 2.24 | 2.07 |

The SEM images of the surface of the dry powder particles of the invention are shown in FIGS. 1 and 2. FIG. 1 shows two views of the size and structure of the spray dried emulsion polymerized microparticles. FIG. 2 shows two views of the size and structure of the coagulated and dried microparticles. In both cases, the dried microparticles have coalesced to form the random microporous structure of the acrylic polymer particles of the invention. FIG. 1b shows that in some areas the spray dried emulsion particles form a pseudo hexagonal close packed arrangement. However, FIGS. 2a and 2b show that although the microporous structure of the coagulated and dried microparticles particles are indistinguishable from the spray dried powder particles, there is no evidence of a hexagonal close packed structure. Not shown in the SEM figures is that the microparticles form discrete larger particles of the first type according to the invention.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A hardenable two part acrylic composition comprising an acrylic polymer composition first part and an acrylic monomer composition second part, the acrylic polymer composition comprising a first type of acrylic polymer particles wherein each first type of acrylic polymer particle is formed of a network of coalesced emulsion polymerized acrylic microparticles.

2. A hardenable two part acrylic composition according to claim 1, wherein the acrylic polymer composition also comprises at least one further type of acrylic polymer particles.

3. A hardenable two part acrylic composition according to claim 2, wherein the at least one further type of acrylic polymer particles are polymer beads.

4. A hardenable two part acrylic composition according to claim 1, wherein the Z-average particle size of the emulsion polymerized microparticles is less than 2000 nm.

5. A hardenable two part acrylic composition according to claim 1, wherein the Z-average particle size of the emulsion polymerized microparticles is between 10-2000 nm.

6. A hardenable two part acrylic composition according to claim 1 wherein the emulsion polymerized microparticles are single stage or multistage core/shell microparticles.

7. A hardenable two part acrylic composition according to claim 1 wherein the emulsion microparticles incorporate an unreacted initiator in their polymer matrix.

8. A hardenable two part acrylic composition according to claim 7, wherein the level of unreacted initiator is 0.001-10% w/w of the emulsion polymerized acrylic microparticles.

9. A hardenable two part acrylic composition according to claim 7, wherein the microparticles are core/shell microparticles and the unreacted initiator is incorporated in the outer shell of the core/shell particles.

10. A hardenable two part acrylic composition according to claim 1 wherein the network of coalesced emulsion polymerized microparticles form a porous acrylic polymer particle.

11. A hardenable two part acrylic composition according to claim 10, wherein the acrylic polymer particle is microporous.

12. A hardenable two part acrylic composition according to claim 1 wherein the acrylic first type of polymer particles of the invention are formed by drying of the liquid emulsion to form a powder.

13. A hardenable two part acrylic composition according to claim 12, wherein the drying is by spray drying, paddle drying, oven drying or drying following coagulation and filtration.

14. A hardenable two part acrylic composition according to claim 1 wherein the weight average molecular weight (Mw) of the emulsion microparticles is between 25,000 daltons and 3,000,000 daltons.

15. A hardenable two part acrylic composition comprising an acrylic polymer composition first part and an acrylic monomer composition second part, the acrylic polymer composition comprising acrylic polymer particles, wherein at least a first type of acrylic polymer particle is microporous.

16. A hardenable two part acrylic composition comprising an acrylic polymer composition first part and an acrylic monomer composition second part, the acrylic polymer composition comprising emulsion polymerised acrylic polymer particles of particle size between 10 and 2000 nm.

17. A hardenable two part acrylic composition according to claim 1, wherein the acrylic polymer composition first part is a powder.

18. A hardenable two part acrylic composition according to claim 17, wherein the weight ratio of powder component to monomer component is generally <3:1.

19. A method of producing an acrylic polymer composition comprising the steps of:
 (a) emulsion polymerizing an acrylic monomer composition to produce a polymer emulsion;
 (b) drying the polymer emulsion of step (a) to produce acrylic polymer particles according to claim 1; and
 (c) optionally, mixing the acrylic polymer particles of step (b) with at least one further type of acrylic polymer particles and/or filler to produce an acrylic polymer composition suitable for hardening at a predetermined rate in the presence of an acrylic monomer composition.

20. A method according to claim 19, wherein step (a) comprises seed, core and at least one shell emulsion polymerisation step.

21. A method according to claim 19, wherein an excess of initiator is introduced into the emulsion polymerization step (a) so that residual initiator is encapsulated within the emulsion particles.

22. A method according to claim 21, wherein the excess initiator is introduced at a sufficiently late stage in the emulsion polymerization to avoid thermal decomposition before encapsulation in the formed polymer particles.

23. A method according to claim 21, wherein the excess initiator is added together with and/or subsequent to at least a portion of initiator to be reacted with monomer in the emulsion polymerization step.

24. A method according to claim 21, wherein at least some of the initiator to be reacted in the emulsion polymerization step is different to the excess initiator and has a shorter half life to thereby preferentially react with monomer in the presence of the excess initiator.

25. A method according to claim 21, wherein in a multi-stage emulsion polymerization, the excess initiator is introduced during the final stage so that it is present in the outer shell of the multistage particle.

26. A powder composition for use as a first part of a hardenable two part acrylic composition comprising a first type of acrylic polymer particles wherein each first type of acrylic polymer particle is formed of a network of coalesced emulsion polymerized acrylic microparticles, and optionally, at least one further type of acrylic polymer particles blended therewith.

27. A powder composition according to claim 26, wherein the emulsion particles of the powder composition incorporate a suitable initiator compound in their polymer matrix.

28. A hardenable two part acrylic composition according to claim 1, wherein the emulsion polymerized acrylic microparticles are free from impact modifier co-monomer residues.

29. A hardenable two part acrylic composition according to claim 1, wherein the first type of acrylic polymer particles have an average particle size of 1-300 microns.

* * * * *